United States Patent
Case et al.

(10) Patent No.: US 7,503,928 B2
(45) Date of Patent: Mar. 17, 2009

(54) ARTIFICIAL VALVE WITH CENTER LEAFLET ATTACHMENT

(75) Inventors: Brian C. Case, Lake Villa, IL (US); Joseph F. Obermiller, West Lafayette, IN (US)

(73) Assignees: Cook Biotech Incorporated; Cook Incorporated

( * ) Notice: Subject to any disclaimer, the term of this patent is extended or adjusted under 35 U.S.C. 154(b) by 148 days.

(21) Appl. No.: 11/582,248

(22) Filed: Oct. 17, 2006

(65) Prior Publication Data

US 2007/0093887 A1    Apr. 26, 2007

Related U.S. Application Data

(60) Provisional application No. 60/729,260, filed on Oct. 21, 2005.

(51) Int. Cl.
A61F 2/06    (2006.01)
A61F 2/24    (2006.01)

(52) U.S. Cl. ..................................................... 623/1.24

(58) Field of Classification Search .................. 623/1.24, 623/1.25, 1.26, 2.1–2.19; A61F 2/06, 2/24
See application file for complete search history.

(56) References Cited

U.S. PATENT DOCUMENTS

| | | | |
|---|---|---|---|
| 4,675,361 A | 6/1987 | Ward et al. | |
| 4,861,830 A | 8/1989 | Ward et al. | |
| 4,902,508 A | 2/1990 | Badylak et al. | |
| 5,017,664 A | 5/1991 | Grasel et al. | |
| 5,405,381 A | 4/1995 | Olin | |
| 5,413,599 A | 5/1995 | Imachi et al. | |
| 5,554,389 A | 9/1996 | Badylak et al. | |
| 5,589,563 A | 12/1996 | Ward et al. | |
| 5,690,642 A | 11/1997 | Osborne et al. | |
| 5,814,061 A | 9/1998 | Osborne et al. | |
| 5,993,844 A | 11/1999 | Abraham et al. | |
| 6,099,567 A | 8/2000 | Badylak et al. | |
| 6,126,686 A * | 10/2000 | Badylak et al. | 623/1.24 |
| 6,206,931 B1 | 3/2001 | Cook et al. | |
| 6,287,334 B1 | 9/2001 | Moll et al. | |
| 6,371,961 B1 | 4/2002 | Osborne et al. | |
| 6,503,272 B2 | 1/2003 | Duerig et al. | |
| 6,508,833 B2 | 1/2003 | Pavcnik et al. | |
| 6,752,826 B2 | 6/2004 | Holloway et al. | |
| 6,939,377 B2 | 9/2005 | Jayaraman et al. | |
| 7,338,520 B2 * | 3/2008 | Bailey et al. | 623/1.24 |
| 2001/0039450 A1 | 11/2001 | Pavcnik et al. | |

(Continued)

FOREIGN PATENT DOCUMENTS

WO    WO/2001/28459 A1    10/2000

(Continued)

OTHER PUBLICATIONS

PCT Search Report for PCT/US2006/041075.

*Primary Examiner*—Brian E. Pellegrino
*Assistant Examiner*—Jason-Dennis Stewart
(74) *Attorney, Agent, or Firm*—Brinks Hofer Gilson & Lione

(57) ABSTRACT

The present invention provides self-expanding or otherwise expandable artificial valve prostheses for deployment within a bodily passageway, such as a vessel or duct of a patient. The valve prostheses include a support structure having an outer frame and supporting a valve leaflet.

20 Claims, 9 Drawing Sheets

U.S. PATENT DOCUMENTS

| | | |
|---|---|---|
| 2002/0065552 A1 | 5/2002 | Jayaraman et al. |
| 2002/0138135 A1 | 9/2002 | Duerig et al. |
| 2002/0187288 A1 | 12/2002 | Lin et al. |
| 2003/0014126 A1 | 1/2003 | Patel et al. |
| 2003/0023300 A1* | 1/2003 | Bailey et al. ............... 623/1.13 |
| 2003/0125795 A1 | 7/2003 | Pavcnic et al. |
| 2003/0149471 A1 | 8/2003 | Briana et al. |
| 2004/0019374 A1 | 1/2004 | Hojeibane et al. |
| 2004/0034409 A1 | 2/2004 | Heublein et al. |
| 2004/0039436 A1* | 2/2004 | Spenser et al. ............ 623/1.13 |
| 2004/0073297 A1 | 4/2004 | Rohde et al. |
| 2004/0180042 A1 | 9/2004 | Cook et al. |
| 2004/0186558 A1 | 9/2004 | Pavcnik et al. |
| 2004/0210301 A1* | 10/2004 | Obermiller ................. 623/1.24 |
| 2004/0225352 A1 | 11/2004 | Osborne et al. |
| 2004/0260389 A1 | 12/2004 | Case et al. |
| 2006/0265053 A1 | 11/2006 | Hunt |
| 2007/0027535 A1 | 2/2007 | Purdy et al. |

FOREIGN PATENT DOCUMENTS

| | | |
|---|---|---|
| WO | WO/2001/049213 | 7/2001 |
| WO | WO 2003/002165 A1 | 1/2003 |
| WO | WO/2003/030782 | 4/2003 |
| WO | WO 2004/080352 A1 | 9/2004 |
| WO | WO 2004/089253 A1 | 10/2004 |

* cited by examiner

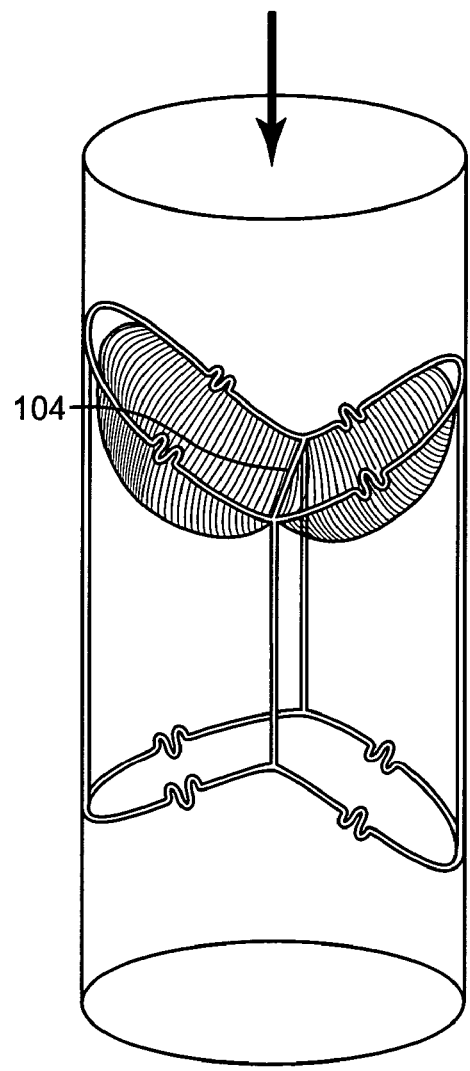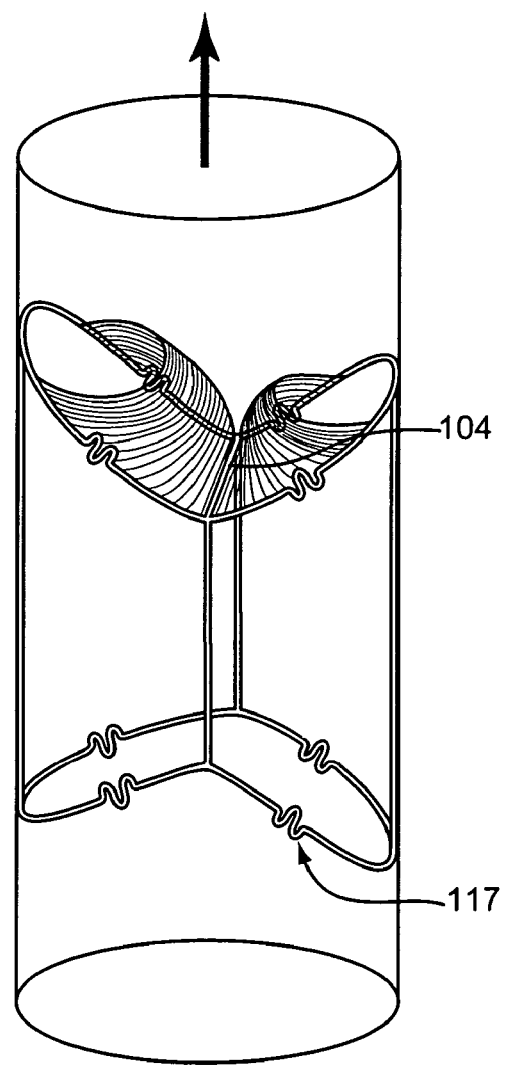

US 7,503,928 B2

ARTIFICIAL VALVE WITH CENTER LEAFLET ATTACHMENT

RELATED APPLICATIONS

This non-provisional patent application claims priority to U.S. Provisional Patent Application No. 60/729,260, filed Oct. 21, 2005, the contents of which are incorporated by reference in their entirety.

TECHNICAL FIELD

This invention relates to medical devices, more particularly to artificial valve prostheses and the like.

BACKGROUND

Many vessels in animals transport fluids from one bodily location to another. In some vessels, such as mammalian veins, natural valves are positioned along the length of the vessel to permit fluid flow in a substantially unidirectional manner along the length of the vessel. These natural valves are particularly important in the lower extremities to prevent blood from pooling in the lower legs and feet during situations, such as standing or sitting, when the weight of the column of blood in the vein can act to prevent positive blood flow toward the heart. A condition, commonly known as "chronic venous insufficiency", is primarily found in individuals where gradual dilation of the veins, thrombotic events, or other conditions prevent the leaflets of the native valves from closing properly. This leads to significant leakage of retrograde flow such that the valve is considered "incompetent". Chronic venous insufficiency is a potentially serious condition in which the symptoms can progress from painful edema and unsightly spider or varicose veins to skin ulcerations. Elevation of the feet and compression stockings can relieve symptoms, but do not treat the underlying disease. Untreated, the disease can impact the ability of individuals to maintain their normal lifestyle.

To treat venous valve insufficiency, a number of surgical procedures have been employed to improve or replace the native valve, including placement of artificial valve prostheses. These efforts have met with limited success and have not been widely adopted as methods of treating chronic venous insufficiency. More recently, efforts have been directed towards finding a suitable self-expanding or radially-expandable artificial valve prostheses that can be placed using minimally invasive techniques, rather than requiring open surgery and its obvious disadvantages. Thus far, use of prosthetic venous valves has remained experimental only.

Prosthetic valves have been developed that use a support frame such as a stent. Frequently, a graft member is attached to the support frame and provides a valve function to the device. For example, the graft member can be in the form of a leaflet that is attached to a stent and movable between first and second positions. In a first position, the valve is open and allows fluid flow to proceed through a vessel in a first direction, and in a second direction the valve is closed to restrict fluid flow in a second, opposite direction. Examples of such prosthetic valves are described in commonly owned U.S. Pat. No. 6,508,833, filed Mar. 21, 2001, and U.S. Publication No. 2004/0186558, published Sep. 23, 2004. Another example of a prosthetic valve assembly, including a valve seat and a movable valve composed of a flexible member, is provided by U.S. Pat. No. 5,413,599, filed Dec. 13, 1999.

Prosthetic valves are designed to replace or supplement the function of incompetent natural valves. The use of an expandable support frame in valve devices allows for the use of minimally invasive delivery devices and techniques for placement of the valves within body vessels, which will likely lower the overall cost of treatment and increase the acceptance of these medical devices by practitioners and patients alike.

SUMMARY

The present invention provides artificial valve prostheses, such as artificial venous valves, having a valve structure and a self-expanding or otherwise expandable support structure. In one embodiment, the present invention provides a valve prosthesis for regulating fluid flow through a body vessel. The valve prosthesis includes a support structure having an outer frame defining a lumen and a transverse member dividing the lumen into a first lumen segment and a second lumen segment. The valve prosthesis also includes a first and a second valve leaflet. Portions of the perimeter of the valve leaflets are attached to the transverse member and to the outer frame proximal of the transverse member to form a enclosure and having a proximal opening defined by the portions of a perimeter of the valve leaflets attached to the outer frame and by portions of the perimeter of the valve leaflets not attached to the outer frame.

The first valve leaflet is positioned within the first lumen segment and the second valve leaflet is positioned within the second lumen segment. The valve leaflets are deformable between a first position allowing fluid flow in a first, antegrade, direction and a second position restricting fluid flow in a second, retrograde, direction.

Another embodiment of the invention provides an artificial valve having a support structure including an outer frame defining a lumen with two ends, two valve leaflets joined at one end to form a joined end, which extends across the lumen near one end of the lumen and divides the lumen into two portions, each leaflet having an end partially attached to the outer frame near the end of the lumen opposite the joined end and two sides attached along a length of the outer frame. The leaflets are deformable between a first position that permits fluid flow in an antegrade direction through the blood vessel and a second position that restricts fluid flow in a retrograde direction.

In one embodiment, support structure includes a polymeric material. In other embodiments, the support structure includes a material selected from a group consisting of stainless steel, nickel, silver, platinum, gold, titanium, tantalum, iridium, tungsten, self-expanding nickel titanium alloys, and inconel.

In one embodiment, the valve leaflets include a material selected from the group consisting of a synthetic biocompatible polymer, cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material, polytetrafluoroethylene, or mixtures or copolymers thereof; polylactic acid, polyglycolic acid or copolymers thereof, a polyanhydride, polycaprolactone, polyhydroxy-butyrate valerate, polyhydroxyalkanoate, a polyetherurethane urea, naturally derived or synthetic collagenous material, an extracellular matrix material, submucosa, small intestinal submucosa, stomach submucosa, urinary bladder submucosa, uterine submucosa, renal capsule membrane, dura mater, pericardium, serosa, peritoneum or basement membrane materials, and liver basement membrane.

In one embodiment, the artificial valve prosthesis includes a support structure having an outer frame defining a lumen and a plurality of radial members each having a first end and a second end. The first ends of the radial members are joined within the lumen and the second end of each of the radial members is attached to the outer frame at positions proximal of the first ends of the radial members. The valve prosthesis also includes a plurality of valve leaflets. A first portion of the perimeter of each of the valve leaflets is attached to adjacent radial members and a second portion of the perimeter of each of the valve leaflets extends between the adjacent radial members. The valve leaflets form an enclosure and having a proximal opening defined by the portions of the perimeter of the valve leaflets extending between the radial members. Each of the plurality of valve leaflets is deformable between a first position allowing fluid flow in a first, antegrade, direction and a second position restricting fluid flow in a second, retrograde, direction.

In one embodiment, the artificial valve prosthesis includes a support structure having an outer frame defining a lumen with two ends and two leaflets joined at one end. The joined end of the valve leaflets extends across the lumen near one end of the lumen so as to divide the lumen into two portions. Each valve leaflet has an end partially attached to the outer frame near the end of the lumen opposite the joined end and two sides attached along a length of the outer frame. The valve leaflets are deformable between a first position that permits fluid flow in an antegrade direction through the blood vessel and a second position that restricts fluid flow in a retrograde direction.

In yet another embodiment, the present invention provides a method of treating a subject. The method includes delivering an artificial valve prosthesis of the present invention to a region of a body vessel in a compressed state and deploying the valve prosthesis in an expanded state.

BRIEF DESCRIPTION OF THE DRAWINGS

Embodiments of the present invention will now be described by way of example with reference to the accompanying drawings.

FIG. 1(a) depicts a valve prosthesis having two valve leaflets positioned to restrict retrograde fluid flow. FIG. 1(b) depicts a valve prosthesis having two valve leaflets positioned to allow antegrade fluid flow. FIGS. 1(c) and 1(d) are schematic views of another illustrative embodiment of the present invention. FIG. 1(c) depicts a valve prosthesis having two valve leaflets positioned to restrict retrograde fluid flow. FIG. 1(d) depicts a valve prosthesis having two valve leaflets positioned to allow antegrade fluid flow. FIG. 1(e) depicts a valve prosthesis having two valve leaflets positioned to restrict retrograde fluid flow. FIG. 1(f) depicts a valve prosthesis having two valve leaflets positioned to allow antegrade fluid flow.

FIG. 2 is a schematic view of another illustrative embodiment of the present invention.

FIG. 3 is a schematic view of yet another illustrative embodiment of the present invention.

DETAILED DESCRIPTION

Definitions

Figures 1A, 1B:
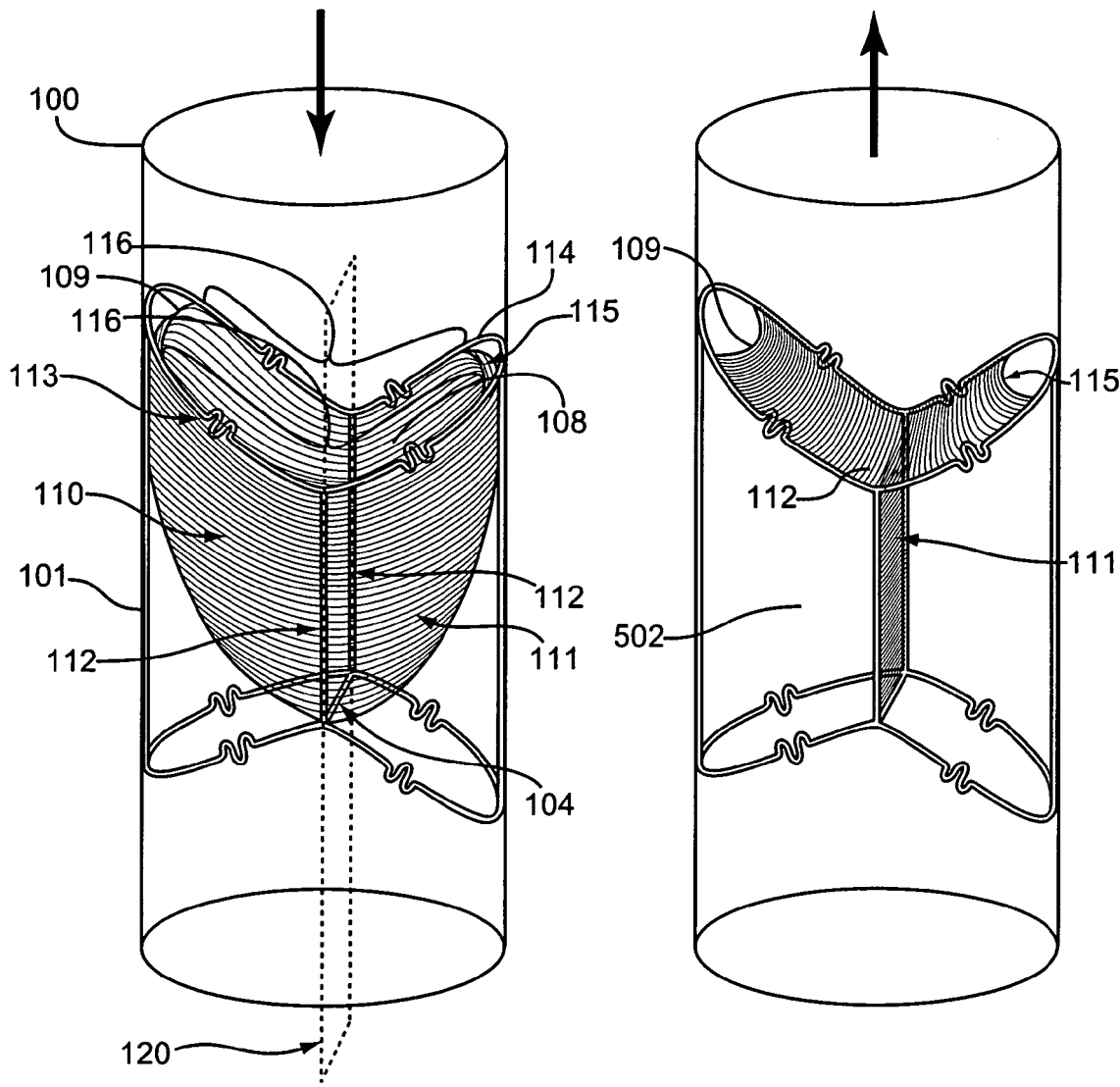
FIGS. 1(a) and 1(b) are schematic views of an illustrative embodiment of the present invention.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

The term "implantable" refers to an ability of a medical device to be positioned at a location within a body, such as within a body vessel. Furthermore, the terms "implantation" and "implanted" refer to the positioning of a medical device at a location within a body, such as within a body vessel.

An "alloy" is a substance composed of two or more metals or of a metal and a nonmetal united, such as by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

A "biodegradable" material is a material that dissipates upon implantation within a body, independent of the mechanisms by which dissipation can occur, such as dissolution, degradation, absorption and excretion. The actual choice of which type of materials to use may readily be made by one of ordinary skill in the art. Such materials are often referred to by different terms in the art, such as "bioresorbable," "bioabsorbable," or "biodegradable," depending upon the mechanism by which the material dissipates. The prefix "bio" indicates that the erosion occurs under physiological conditions, as opposed to other erosion processes, caused for example, by high temperature, strong acids or bases, UV light or weather conditions.

A "biocompatible" material is a material that is compatible with living tissue or a living system by not being toxic or injurious and not causing immunological rejection.

A "non-bioabsorbable" or "biostable" material refers to a material, such as a polymer or copolymer, which remains in the body without substantial dissipation.

A "remodelable material" is a material that, when implanted in vivo, is capable of being resorbed by the body or providing a matrix for the regrowth of autologous cells. In some embodiments, fluid contacting autologous cells on an implanted remodelable material interface can affect the growth of autologous tissue on the implanted remodelable material.

The phrase "controlled release" refers to the release of an agent at a predetermined rate. A controlled release may be constant or vary with time. A controlled release may be characterized by a drug elution profile, which shows the measured rate that the agent is removed from a device in a given solvent environment as a function of time. For example, a controlled release elution profile from a valve prosthesis may include an initial burst release associated with the deployment of the valve prosthesis, followed by a more gradual subsequent release. A controlled release may be a gradient release in which the concentration of the agent released varies over time or a steady state release in which the agent is released in equal amounts over a certain period of time (with or without an initial burst release).

As used herein, the phrase "bioactive agent" refers to any pharmaceutically active agent that produces an intended therapeutic effect on the body to treat or prevent conditions or diseases.

Implantable Valve Prostheses

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

Devices and systems of the invention are desirably adapted for deployment within a body lumen, and in particular embodiments, devices and systems of the invention are adapted for deployment within the venous system. Accordingly, preferred devices adapted are venous valves, for example, for percutaneous implantation within veins of the legs or feet to treat venous insufficiency.

One aspect of the present invention provides a self-expanding or otherwise expandable artificial valve prosthesis for deployment within a bodily passageway, such as a vessel or duct of a patient. The prosthesis is typically delivered and implanted using well-known transcatheter techniques for self-expanding or otherwise expandable prostheses. The valve prosthesis is positioned so as to allow antegrade fluid flow and to restrict retrograde fluid flow. Antegrade fluid flow travels from the distal (upstream) end of the prosthesis to the proximal (downstream) end of the prosthesis, the latter being located closest to the heart in a venous valve when placed within the lower extremities of a patient.

The valve prostheses of the present invention include a support structure and one or more valve leaflets. The valve leaflets are positioned within a vessel and supported by the support structure. The support structure includes an outer frame that, when positioned in a body vessel, generally conforms to the shape of the vessel wall and defines a lumen within the vessel. The support structure also includes one or more members positioned within the lumen and connected to the outer frame. For the purposes of the invention, a "radial member" is a member of the support structure that extends from the outer frame into the lumen on the vessel. A "transverse member" is a member of the support structure that extends from the outer frame across the lumen on the vessel.

The valve leaflets are configured to deform to selectively allow fluid flow in an antegrade direction and to restrict fluid in a retrograde direction by opening or closing in response to changes in the fluid pressure differential within the vessel, such as in the presence of retrograde flow.

Illustrative Valve Prostheses

FIGS. 1(a) and 1(b) depict an illustrative embodiment of an artificial valve prosthesis of the present invention. The artificial valve prosthesis includes a support structure having an outer frame 101 defining a lumen and supporting at least one transverse member 104 traversing the lumen and dividing the lumen into two segments. Portions of the perimeter of valve leaflets 110 and 111 are attached to transverse member 104 and to the outer frame 101. Valve leaflet 110 is positioned in one lumen segment and valve leaflet 111 in the other lumen segment. A valve leaflet is positioned within a particular lumen segment when it is positioned in a portion of the lumen defined by a segment of the vessel wall and a plane 120 formed by the transverse member 104 and the distal-proximal axis of the outer frame of the valve prosthesis.

In one embodiment, transverse member 104 includes at least one curved portion configured to allow this member to transform from a collapsed and an expanded state during deployment of the artificial valve prosthesis. Alternatively, transverse member 104 may include telescopic elements that expand during deployment of the artificial valve prosthesis.

In one embodiment, valve leaflets 110 and 111 are attached to the outer frame downstream (with respect to antegrade flow) to the region of attachment to transverse member 104. FIGS. 1(a) and 1(b) illustrate such an attachment. Valve leaflet 110 is attached to the outer frame 101 at members 112 and 113 and valve leaflet 111 is attached to the outer frame at members 112 and 114. Portion 109 of the perimeter of valve leaflet 110 and portion 115 of the perimeter of valve leaflet 111 are not attached to the outer frame or to transverse member 104. The attachment of valve leaflets 110 and 111 to the transverse member 104 and to the outer frame 112 is such that the valve leaflets form an enclosure 108 having a opening facing the proximal end of the valve prosthesis and defined by portions 116 of a perimeter of the valve leaflets attached to the outer frame and by free portions 109 and 115 of the perimeter of the valve leaflets.

When positioned with a vessel 100, valve leaflets 110 and 111 are deformable, in response to the direction of fluid flow within the vessel, between a first position allowing fluid flow in a first, antegrade, direction to a second position restricting fluid flow in a second, retrograde, direction. In FIG. 1(a), the valve leaflets are positioned so as to restrict fluid flow in a retrograde direction. Here, portions of the valve leaflets adjacent to perimeter portions 109 and 115 are positioned towards the wall of vessel 100.

In FIG. 1(b), valve leaflets 110 and 111 are positioned to allow fluid flow in an antegrade direction. In this configuration, the bodies of valve leaflets 110 and 111 are positioned closer together. Perimeter portions 109 and 115 are positioned away from the wall of vessel 100 so as to form an opening in each lumen segment and hence allowing antegrade fluid flow.

FIGS. 1(c) and 1(d) depict another illustrative embodiment of an artificial valve prosthesis of the present invention. In this embodiment, transverse member 104 is positioned closer to the proximal (downstream) end of the prosthesis and the valve leaflets are not attached to members 112. Valve prostheses of the present invention may include one of more fillits 117 comprising one or more bends. Fillets are well known in the valve prosthesis art as a means to reduce stresses in bends positioned to allow radial compression of the prosthesis frame. Further examples of fillets are disclosed in copending patent U.S. patent application Ser. No. 10/642,372 entitled, Implantable Vascular Device, filed Aug. 15, 2003, the contents of which are incorporated herein by reference.

Figure 1E:
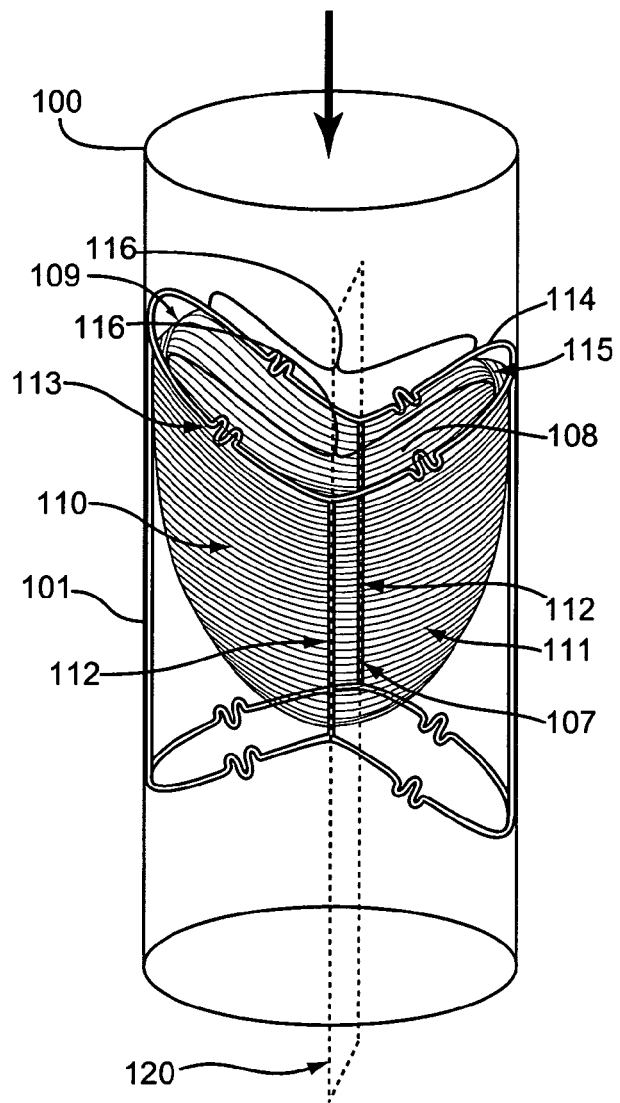
FIGS. 1(e) and 1(f) are schematic views of another illustrative embodiment of the present invention.
Figure 1F:
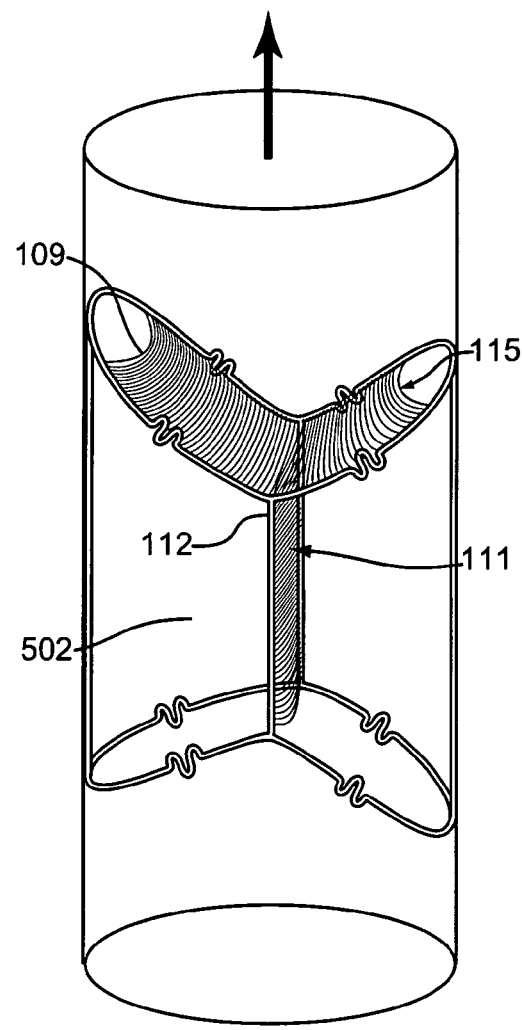

FIGS. 1(e) and 1(f) depict another illustrative embodiment of an artificial valve prosthesis of the present invention. In this embodiment, transverse member 104 is not present. Instead, portions of the perimeter of valve leaflets 110 and 111 are joined to each other to form a continuous surface, as in illustrated in FIGS. 1(e) and 1(f). Alternatively, valve leaflets 110 and 111 may be formed from a single piece of material that is joined to the outer frame 101 at members 112 and 113.

Figure 2A:
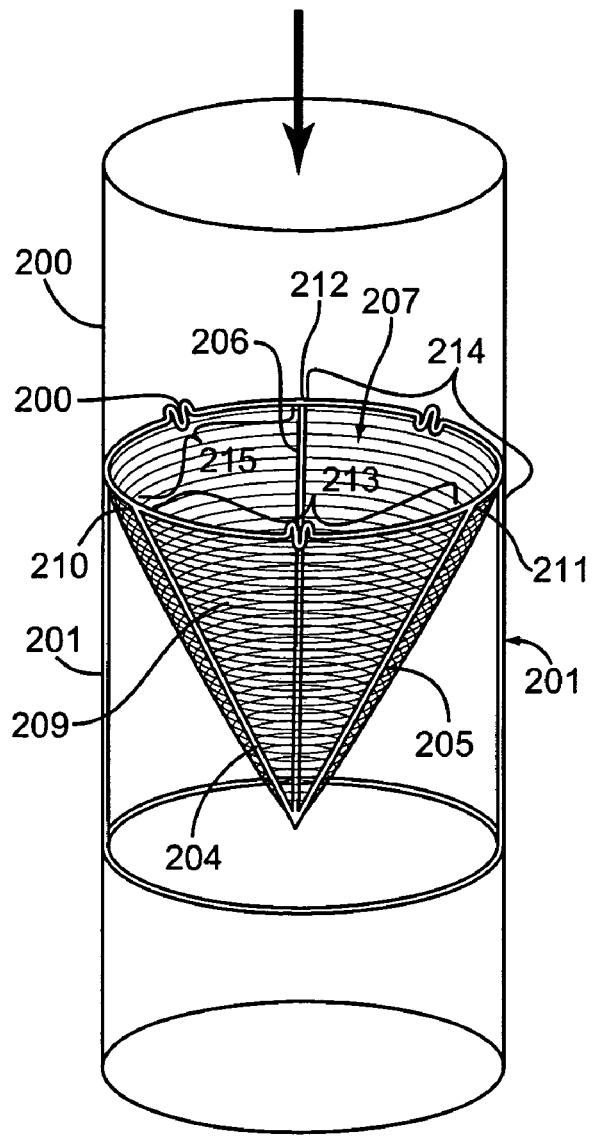
FIG. 2(a) depicts a valve prosthesis having three valve leaflets positioned to restrict retrograde fluid flow.
Figure 2B:
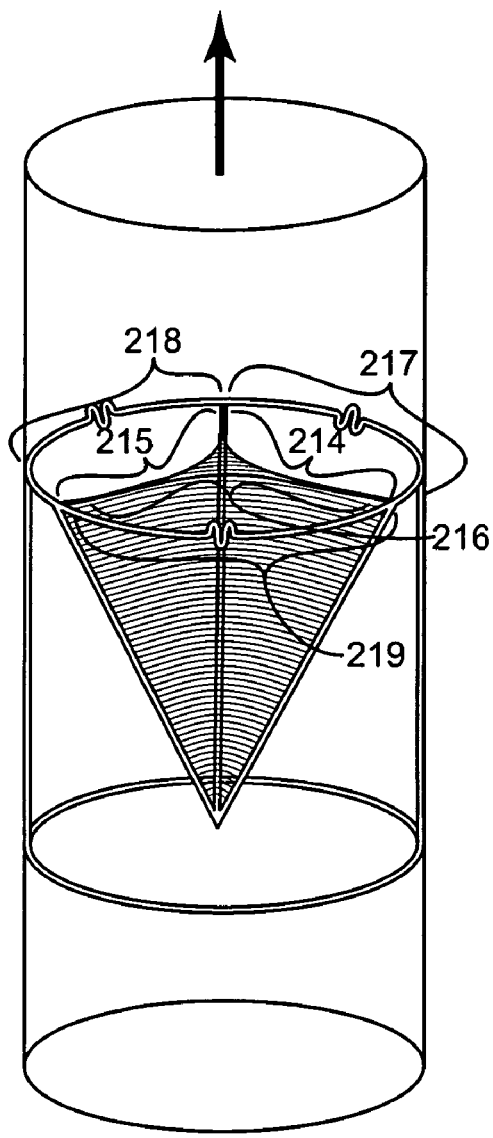
FIG. 2(b) depicts a valve prosthesis having three valve leaflets positioned to allow antegrade fluid flow.

FIGS. 2(a) and 2(b) depict another illustrative embodiment of an artificial valve prosthesis of the present invention. The artificial valve prosthesis includes a support structure having an outer frame 201 defining a lumen and supporting at three radial members 204, 205 and 206 each having a first end joined with the first end of other radial members within the lumen and a second end attached, at positions 210, 211 and 212 respectively, on the circumference of portion 202 of the outer frame 201. The radial members are joined to outer frame 201 at a position proximal to the position of joining of the first ends of the radial members.

Each of valve leaflets 207, 208 and 209 is attached to two adjacent members of radial members 204, 205 and 206 so as to form an enclosure 213 as is illustrated in FIG. 2(a). Portions of the perimeter of valve leaflet 208 are attached to adjacent radial members 204 and 206. Portion 215 of the perimeter of valve leaflet 208 extends between the positions of attachment 210 and 212 and is not attached to the radial members or the outer frame 201. Similarly, portions of the perimeter of valve leaflet 209 are attached to adjacent radial members 204 and 205 and portions of the perimeter of valve leaflet 207 are attached to radial members 205 and 206. Portion 214 of valve leaflet 207 and portion 216 of valve leaflet 209 are not attached to the radial members or the outer frame 201. Enclosure 213 opens towards the proximal end of the valve prosthesis by an opening defined by portions 214, 215 and 216 of the perimeter of valve leaflets 207, 208 and 209 extending between adjacent radial members.

When positioned with a vessel 200, valve leaflets 207, 208 and 209 are deformable, in response to the direction of fluid flow within vessel 200, between a first position allowing fluid flow in a first, antegrade, direction and a second position restricting fluid flow in a second, retrograde, direction. In FIG. 2(a), valve leaflets 207, 208 and 209 are positioned so as to restrict fluid flow in a retrograde direction. Portions 214, 215 and 216 of the perimeter of valve leaflets 207, 208 and 209 are positioned towards the wall of vessel 200.

In FIG. 2(b), valve leaflets 207, 208 and 209 are positioned to allow fluid flow in an antegrade direction. In this configuration, the bodies of valve leaflets 207, 208 and 209 are positioned towards the center of the lumen. Free portions 214, 215 and 216 are positioned away from the wall of the vessel so as to form openings, between free portions 214, 215 and 216 and the corresponding segments of the outer frame 217, 218 and 219 respectively, allowing antegrade fluid flow.

In the embodiment illustrated in FIGS. 2(a) and 2(b), the first ends of the of the radial members 204, 205 and 206 are joined at a common position within the lumen and the second end of each of the radial members is attached to the outer frame at an equal proximal distance from the common position and at positions equally spaced around a circumference of the outer frame. In this embodiment, radial members 204, 205 and 206 are of equal length.

The present invention also includes embodiments where radial members 204, 205 and 206 are not of equal length. In such embodiments, the second end of each of the radial members may be attached to the outer frame at differing proximal distances from the position of joining of the first ends of the radial members. Also, the second ends of the radial members may be attached at positions not equally spaced around a circumference of the outer frame.

Figures 3A, 3B:
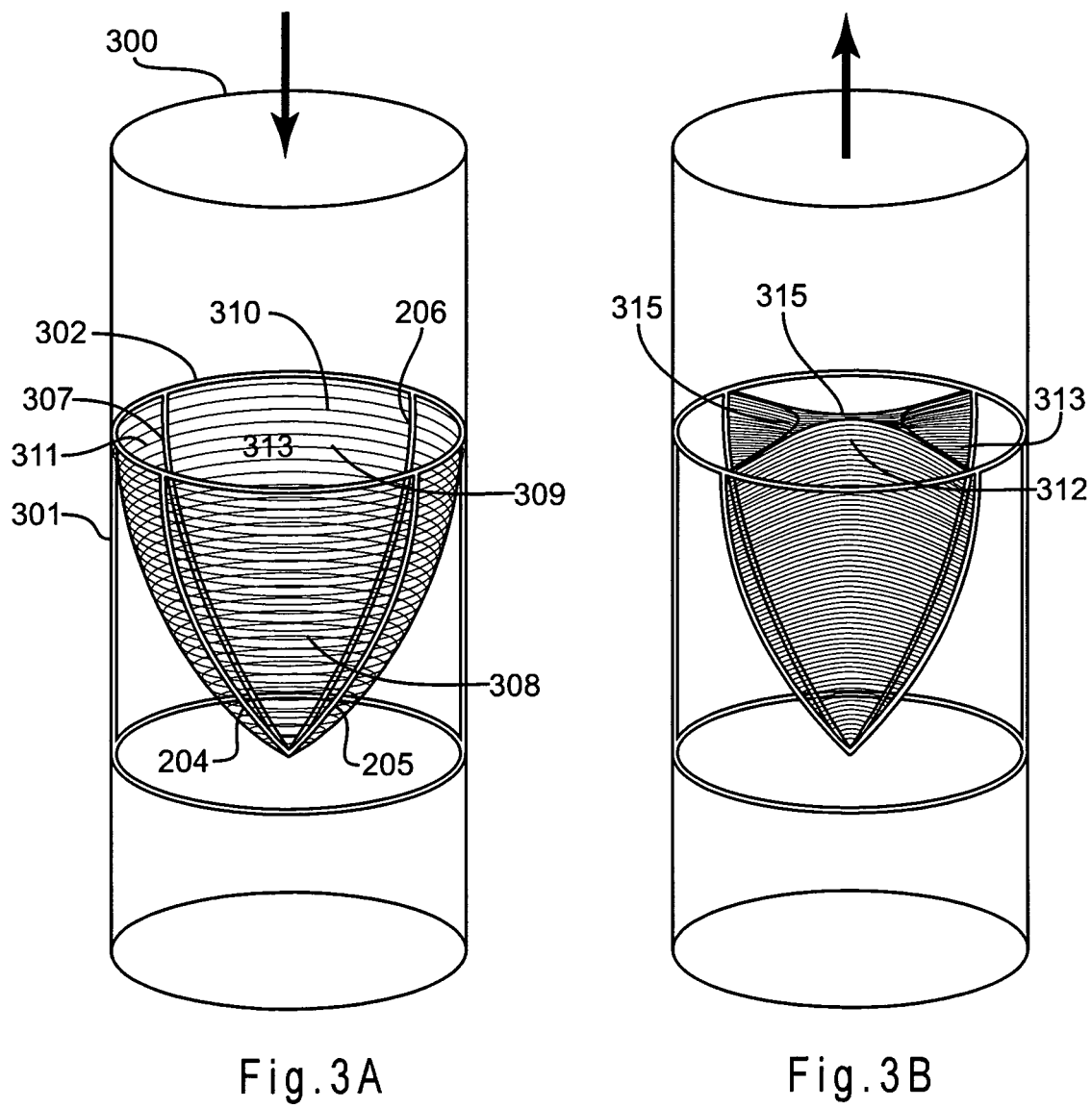
FIG. 3(a) depicts a valve prosthesis having four valve leaflets positioned to restrict retrograde fluid flow.
FIG. 3(b) depicts a valve prosthesis having four valve leaflets positioned to allow antegrade fluid flow.

FIGS. 3(a) and 3(b) illustrate yet another embodiment of an artificial valve prosthesis of the present invention. This embodiment includes a support structure having an outer frame 301 defining a lumen and supporting at four radial members 304, 305, 306 and 307 each having one end joined to the other radial members within the lumen and the other end attached at the circumference of portion 302 of the outer frame 301. The second ends of radial members 304, 305, 306 and 307 are joined to the outer frame at a position proximal to the position of joining of the first ends of the radial members.

As in the case of the valve prosthesis illustrated in FIGS. 2(a) and 2(b), each of valve leaflets is attached to two of radial members so as to form an enclosure 313 as is illustrated in FIG. 3(a). When positioned with a vessel 300, the valve leaflets are deformable, in response to the direction of fluid flow within the vessel, between a first position allowing fluid flow in a first, antegrade, direction to a second position restricting fluid flow in a second, retrograde, direction. In FIG. 3(a), valve leaflets 308, 309, 310 and 311 are positioned so as to restrict fluid flow in a retrograde direction. Free portions of the perimeter of valve leaflets are positioned towards the wall of vessel 300.

In FIG. 3(b), the valve leaflets are positioned to allow fluid flow in an antegrade direction. In this configuration, the bodies of valve leaflets 308, 309, 310 and 311 are positioned towards the center of the lumen. Free portions 312, 313, 314 and 315 are positioned away from the wall of vessel 301 so as to form openings, between these portions and the corresponding segments of the vessel wall, allowing antegrade fluid flow.

In the above embodiments, the amount of slack in the valve leaflet material helps determine how well the valve leaflets restrict retrograde flow and how large of an opening they permit during antegrade flow. In one embodiment of the present invention, the valve prosthesis is configured such that the distance formed between the valve leaflets in their fully open position is such that the cross sectional area available for antegrade fluid flow is between 90 and 10 percent of the cross sectional area of the outer frame in the region of attachment of the valve leaflets to the support frame. In another embodiment, the valve prosthesis is configured such that the cross sectional area available for antegrade fluid flow is between 70 and 30 percent of the cross sectional area of the outer frame in the region of attachment of the valve leaflets to the support frame. In yet another embodiment, the valve prosthesis is configured such that the cross sectional area available for antegrade fluid flow is between 50 and 40 percent of the cross sectional area of the outer frame in the region of attachment of the valve leaflets to the support frame.

Elements shown in the embodiments described herein can be added to and/or exchanged with other embodiments to provide additional embodiments. It will also be understood that other valve body configurations are also contemplated as being within the scope of the present invention. For example, valves having five or more valve leaflets are contemplated. Hence, the number of leaflets possible for embodiments of the present invention can be one, two, three, four, or any practical number, but bi-leaflet valves may prove advantageous in low-flow venous situation as compared to tri-leaflet embodiments, such the type used as heart valves. The valve leaflets may be of equal size and shape or of differing size and shape depending on the configuration of the supporting frame members.

Valve Prosthesis Support Structure

The support structure used in the artificial valve prosthesis of the present invention can be, for example, formed from wire, cut from a section of cannula, molded or fabricated from a polymer, biomaterial, or composite material, or a combination thereof. The pattern (i.e., configuration of struts and cells) of the outer frame, including any anchoring portion(s), which is selected to provide radial expandability to the prosthesis is also not critical for an understanding of the invention. Any support structure is applicable for use with the claimed valve prosthesis so long as this structure supports the valve leaflets in the required position. Numerous examples of support structures are disclosed in copending patent U.S. patent application Ser. No. 10/642,372 entitled, Implantable Vascular Device, filed Aug. 15, 2003, the contents of which are incorporated herein by reference.

Figure 4A:
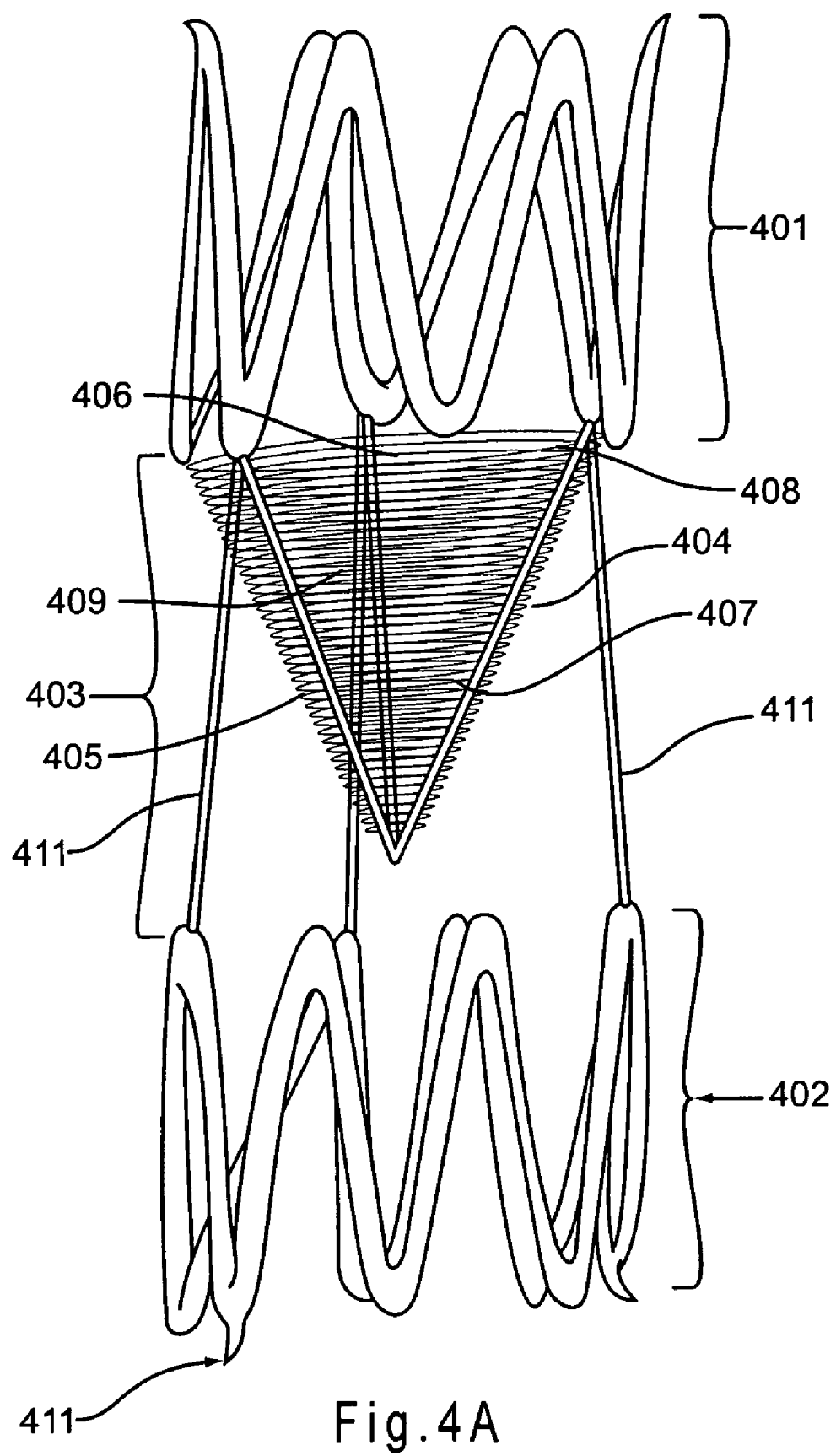
FIG. 4(a) is a schematic view of another illustrative embodiment of the present invention. A valve prosthesis is shown including a support structure having a first section and a second section that are spaced apart from one another, defining an intermediate section containing three radial members and attached valve leaflets.

FIG. 4(a) illustrates an embodiment of the present invention in which the valve prosthesis includes a support structure having a first section 401 and a second section 402 that are spaced apart from one another, defining an intermediate section 403 containing three radial members 404, 405 and 406 and attached valve leaflets 407, 408 and 409. Of course, the present invention encompasses embodiments where two four or more leaflets are present.

Sections 401 and 402, which can comprise a pair of radially expandable or self-expanding anchoring portions, are joined by one or more interconnecting members 411. The radial members 404, 405 and 406 are attached to section 401. In embodiments of the present invention, the anchoring portions may function as stents to help the bodily passage remain open, but their primary function is limited to engaging the bodily passage to the radial members and hence the valve leaflets. The anchoring portions may include one or more barbs 410.

In certain embodiments, the intermediate section 403 is a substantially open section. The term "substantially open section" is used herein to define a largely unsupported portion of the bodily passage in which at least some minimal interconnecting structure is present that traverses the unsupported portion of the bodily passage, but that comprises very limited surface area and typically supplies minimal, if any, force against the walls of the passageway lateral to the valve prosthesis.

The valve prosthesis is configured so that it advantageously expands with the deployment of the proximal and distal sections 401 and 402 and radial members 404, 405 and 406 such that, when positioned by retrograde flow, the outer portions of valve leaflets 407, 408 and 409 are positioned towards the vessel wall sufficiently to at least substantially prevent leakage of bodily fluid around the valve structure.

Figure 4B:
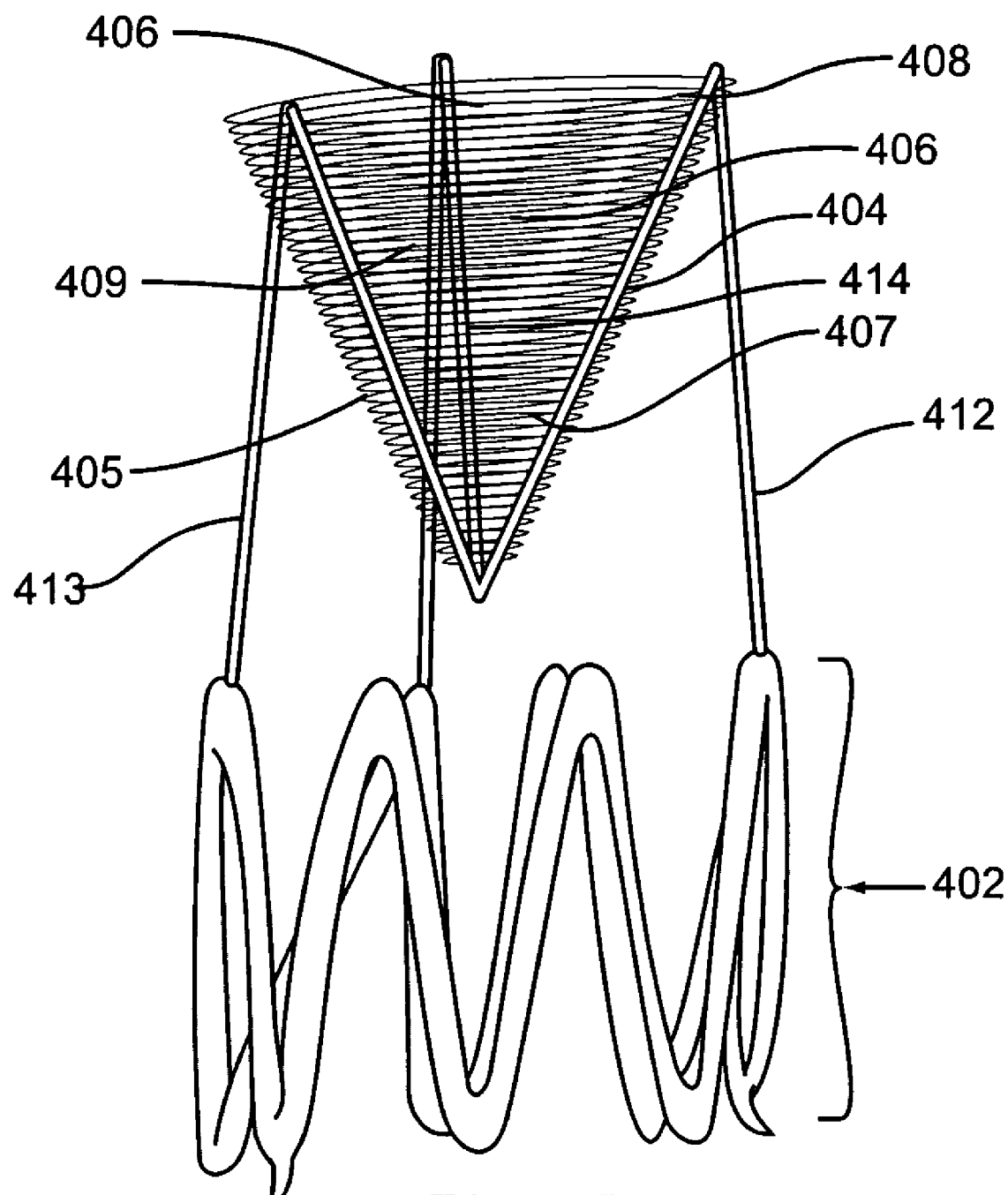
FIG. 4(b) is a schematic view of an illustrative embodiment of the present invention including a support structure having a one section.
Figure 4C:
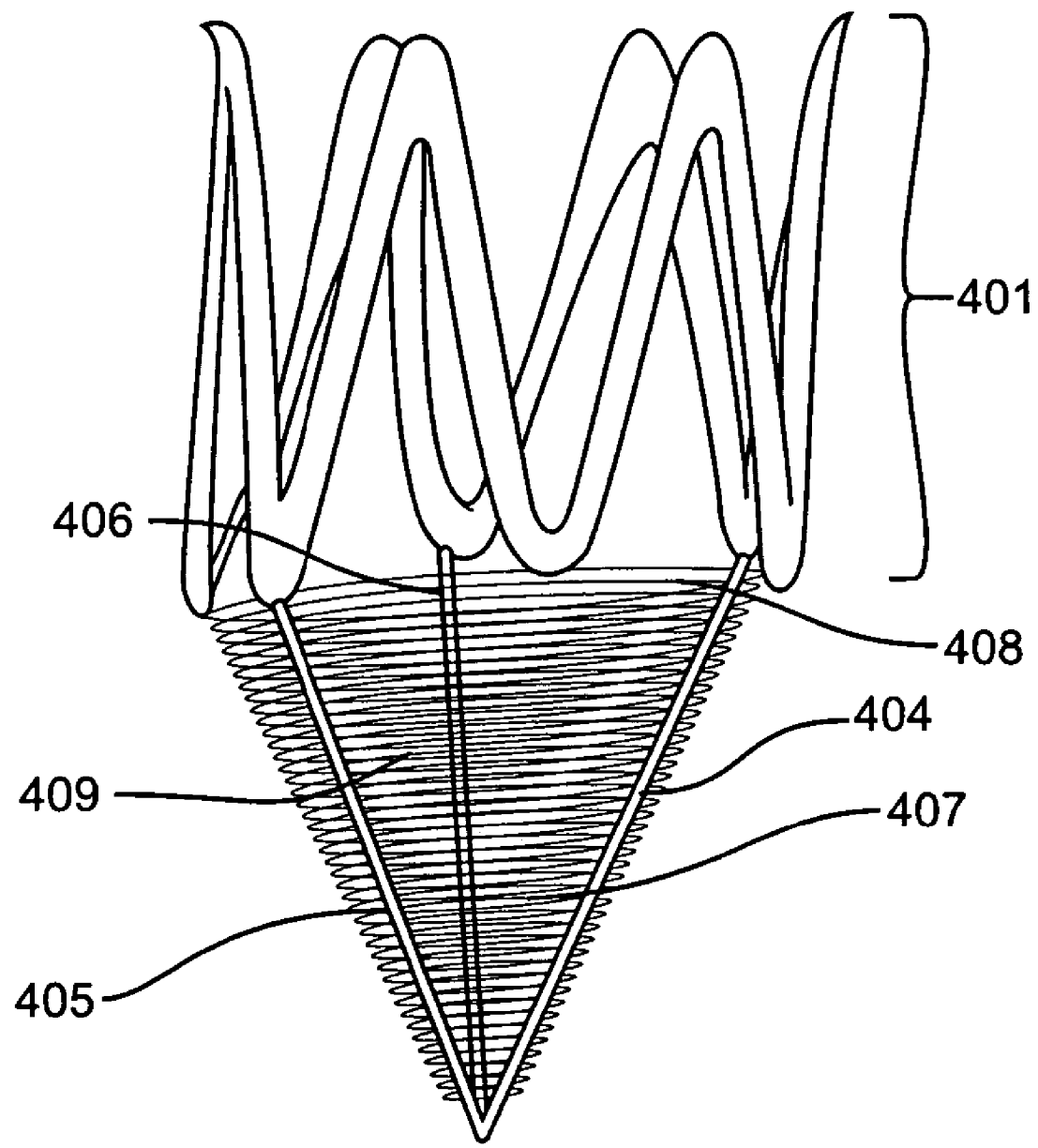
FIG. 4(c) is a schematic view of another illustrative embodiment of the present invention including a support structure having a one section.

The present invention also encompasses embodiments where only one of sections 401 or 402 is present. One such embodiment is illustrated in FIG. 4(b). In this embodiment, interconnecting members 412, 413 and 414 extend from support section 402 to support radial members 404, 405 and 406 respectively. FIG. 4(c) illustrates yet another such embodiment. In this embodiment, a support section 401 is positioned downstream (with respect to antegrade flow) of and attached to radial members 404, 405 and 406.

Controlled Retrograde Flow

The artificial valve prosthesis of the present invention can be configured to permit a controlled amount of retrograde flow through a body vessel despite the presence of the valve prosthesis. This may be desirable for a variety of reasons. For example, allowance of a controlled amount of retrograde flow can assist in the prevention of pooling of fluid when the valve prosthesis is in a closed or substantially closed configuration in the body vessel.

Figure 5A:
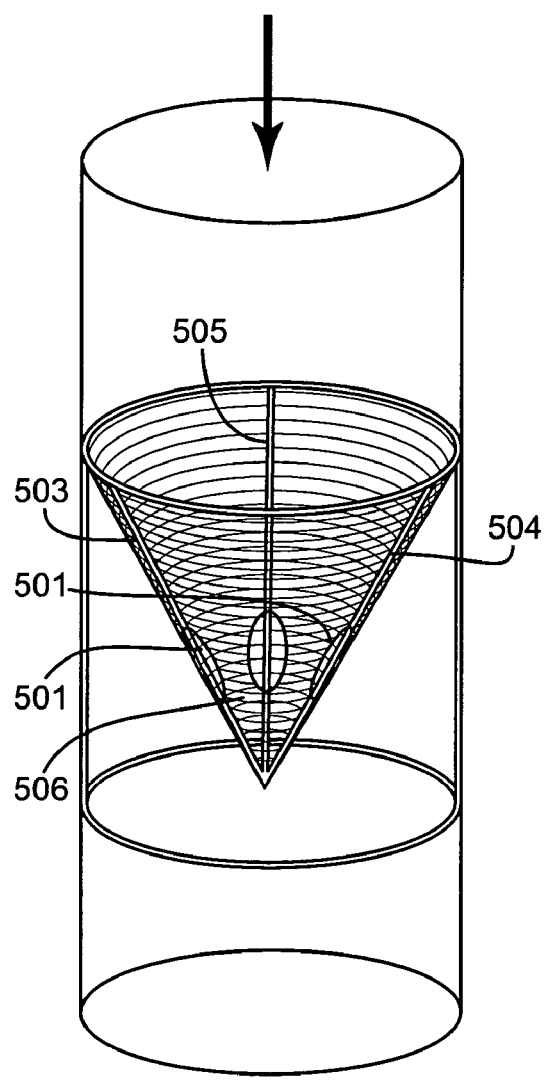
FIGS. 5(a) and 5(b) are schematic views of illustrative embodiments of the present invention depicting valve prostheses allowing for limited retrograde fluid flow.
Figure 5B:
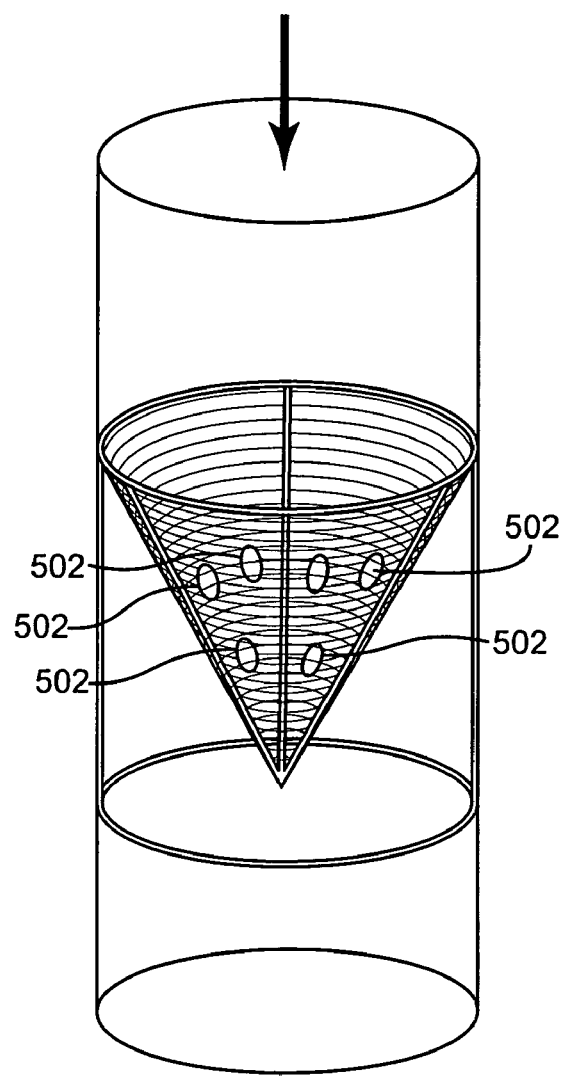

Any suitable means for permitting a controlled amount of retrograde flow to pass through the valve prosthesis can be used in any of the embodiments described herein. FIG. 5 illustrates embodiments of an artificial valve prosthesis that includes suitable means for permitting a controlled amount of retrograde flow. In the embodiment depicted in FIG. 5(a), the valve prosthesis includes three valve leaflets supported by radial members 503, 504 and 505. The valve leaflets are positioned within a vessel to restrict retrograde flow in the vessel. Portions of the perimeter of each valve leaflet attach the leaflet between two of the radial members. For example, valve leaflet 506 is attached between radial members 503 and 504. However, one or more regions of the perimeter of valve leaflet perimeter 501 along radial members 503 and 504 are not attached to these members resulting in the formation of an aperture between portions of the perimeter of the valve leaflet and the corresponding radial member. When the valve leaflets are positioned to restrict retrograde flow, a limited amount of retrograde is therefore permitted. FIG. 5(b) depicts another embodiment of the present invention permitting a controlled amount of retrograde flow. In this embodiment, apertures 502 are present in the body of the valve leaflets of a valve prosthesis having three valve leaflets. When the valve leaflets are positioned to restrict retrograde flow, a limited amount of retrograde is can occur through these apertures.

The present invention contemplates valve prostheses having at least one valve leaflet including one or more apertures in the body of the valve leaflet(s) and or having one or apertures between a portion of the perimeter of one or more valve leaflets and the corresponding radial member or having a combination of such apertures.

The quantity of retrograde flow that passes through an aperture is controlled by the overall dimensions and configuration of the aperture, including the size of the lumen of the aperture. A larger lumen allows a greater amount of retrograde flow to pass through the valve prosthesis while a relatively smaller lumen will allow a relatively lesser amount of retrograde flow to pass. The dimensions and configuration of the aperture of each embodiment can be optimized based upon the vessel in which the valve prosthesis is placed. The size and configuration selected will depend on several factors, including the vessel size, typical flow volumes and rates, and others. The lumen is advantageously sized to allow a desired amount of retrograde flow pass through the lumen during periods of retrograde flow. The aperture should be small enough, though, to still allow the valve prosthesis to substantially prevent retrograde flow when the valve prosthesis is in a closed configuration.

Thus, the aperture is advantageously sized so as to not allow a majority of retrograde flow to pass through the aperture. In one embodiment, the total open area of the aperture is, at a maximum, less than the cross-sectional area of the vessel lumen. As used herein, the term "total open area", in relation to the aperture, refers to the total area of the aperture when the entire perimeter of the aperture lies in the same plane.

The aperture advantageously can be sized to mimic the degree of retrograde flow—the leakiness—that is present in a natural valve located at the point of treatment in the body vessel. Accordingly, the dimensions of the aperture can be determined and optimized based upon the vessel in which the frameless grafting prosthesis is to be placed. For venous valve applications, the total open area of the aperture is advantageously less than about 50% of the cross-sectional area of the vessel at the intended point of deployment. More advantageously, the total open area of the aperture is less than about 25% of the total cross-sectional area of the vessel at the intended point of deployment. In one example, a device is configured for placement in a vessel having a total cross-sectional area of about 50 mm$^2$. In this example, the aperture has a total open area of about 20 mm$^2$. Also for venous valve applications, a circular lumen with a diameter of between about 0.5 and about 3.0 mm has been found to be suitable. In a specific venous valve example, a circular lumen with a diameter of about 1 mm has been found to be suitable. In another specific venous valve example, a circular lumen with a diameter of about 2 mm has been found to be suitable.

The aperture can have any suitable shape. Examples of specifically contemplated shapes include circular, ovoid, triangular, square, rectangular, and tear-drop shaped openings. Furthermore, multiple openings can be used. In these embodiments, the sum total open area of all openings is advantageously in accordance with the parameters described above. Further examples of valves having apertures allowing limited retrograde flow are disclosed in U.S. 2004/0225352A1, published Nov. 11, 2004, the contents of which are incorporated herein by reference.

Support Structure Composition

The materials used in the support structure, including the outer frame and the radial members can be selected from a well-known list of suitable metals and polymeric materials appropriate for the particular application, depending on necessary characteristics that are required (self-expansion, high radial force, collapsibility, etc.). Suitable metals or metal alloys include: stainless steels (e.g., 316, 316L or 304); nickel-titanium alloys including shape memory or superelastic types (e.g., nitinol or elastinite); inconel; noble metals including copper, silver, gold, platinum, paladium and iridium; refractory metals including molybdenum, tungsten, tantalum, titanium, rhenium, or niobium; stainless steels alloyed with noble and/or refractory metals; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; bioabsorbable materials, including magnesium; or other biocompatible metals and/or alloys thereof.

In various embodiments, the support structure comprises a metallic material selected from stainless steel, nickel, silver, platinum, gold, titanium, tantalum, iridium, tungsten, a self-expanding nickel-titanium alloy, a superelastic nickel-titanium alloy sold under the tradename NITINOL or inconel.

One particularly preferred material for forming a frame is a self-expanding material such as the superelastic nickel-titanium alloy sold under the tradename NITINOL. Materials having superelastic properties generally have at least two phases: a martensitic phase, which has a relatively low tensile strength and which is stable at relatively low temperatures, and an austenitic phase, which has a relatively high tensile strength and which can be stable at temperatures higher than the martensitic phase. Shape memory alloys undergo a transition between an austenitic phase and a martensitic phase at certain temperatures. When they are deformed while in the martensitic phase, they retain this deformation as long as they remain in the same phase, but revert to their original configuration when they are heated to a transition temperature, at which time they transform to their austenitic phase. The temperatures at which these transitions occur are affected by the nature of the alloy and the condition of the material. Nickel-titanium-based alloys (NiTi), wherein the transition temperature is slightly lower than body temperature, are preferred for the present invention. It can be desirable to have the transition temperature set at just below body temperature to insure a rapid transition from the martinsitic state to the austenitic state when the frame can be implanted in a body lumen.

Preferably, the support structure comprises a self-expanding nickel titanium (NiTi) alloy material. The nickel titanium alloy sold under the tradename NITINOL is a suitable self-expanding material that can be deformed by collapsing the frame and creating stress which causes the NiTi to reversibly change to the martensitic phase. The support structure can be restrained in the deformed condition inside a delivery sheath typically to facilitate the insertion into a patient's body, with such deformation causing the isothermal phase transformation. Once within the body lumen, the restraint on the support structure can be removed, thereby reducing the stress thereon so that the superelastic support structure returns towards its original undeformed shape through isothermal transformation back to the austenitic phase. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," Scientific American, 281:74-82 (November 1979), incorporated herein by reference.

Some embodiments provide support structures that are not self-expanding, or that do not comprise superelastic materials. For example, in other embodiments, the support structure can comprise silicon-carbide (SiC). For example, published U.S. Patent Application No. US2004/034409 to Hueblein et al., published on Feb. 14, 2004 and incorporated in its entirety herein by reference, discloses various suitable frame materials and configurations.

Other suitable materials used in the support structure include carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these.

Valve Leaflet Composition

The material used in body of the valve leaflets includes a biocompatible material, and is, in one embodiment, a bioremodelable material. Suitable bioremodelable materials may be made from natural or synthetic polymers, including collagen. Thus, in general, the flexible material may comprise a synthetic biocompatible polymer such as cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material such as polytetrafluoroethylene, or mixtures or copolymers thereof; polylactic acid, polyglycolic acid or copolymers thereof, a polyanhydride, polycaprolactone, polyhydroxybutyrate valerate, polyhydroxyalkanoate, or another biodegradable polymer.

In certain embodiments of the invention, the flexible material is comprised of a naturally derived or synthetic collagenous material, and especially an extracellular collagen matrix material. Suitable extracellular matrix materials ("ECM material") include, for instance, submucosa (including, for example, small intestinal submucosa ("SIS"), stomach submucosa, urinary bladder submucosa, or uterine submucosa), renal capsule membrane, dura mater, pericardium, serosa, and peritoneum or basement membrane materials, including liver basement membrane. These layers may be isolated and used as intact natural sheet forms, or reconstituted collagen layers including collagen derived from these materials or other collagenous materials may be used. For additional information as to submucosa materials useful in the present invention, and their isolation and treatment, reference can be made to U.S. Pat. Nos. 4,902,508, 5,554,389, 5,993,844, 6,206,931, and 6,099,567, the contents of which are incorporated herein by reference. Renal capsule tissue can also be obtained from warm blooded vertebrates, as described more particularly in copending U.S. patent application Ser. No. 10/186,150, filed Jun. 28, 2002, and International Patent Application Serial Number PCT/US02/20499, filed Jun. 28, 2002, and published Jan. 9, 2003 as International Publication Number W003002165, the contents of which are incorporated herein by reference.

In one embodiment of the invention, the ECM material is porcine SIS. SIS can be prepared according to the method disclosed in U.S. 2004/0180042A1, published Sep. 16, 2004, the contents of which are incorporated herein by reference.

In certain embodiments of the invention, the valve leaflet material is a biocompatible polyurethane. One example of a biocompatible polyurethane is THORALON (THORATEC, Pleasanton, Calif.), as described in U.S. Pat. Application Publication No. 2002/0065552 A1 and U.S. Pat. No. 4,675,361, both of which are incorporated herein by reference. According to these patents, THORALON is a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide either porous or non-porous THORALON. Porous THORALON can be formed by mixing the polyetherurethane urea (BPS-215), the surface modifying additive (SMA-300) and a particulate substance in a solvent. The particulate may be any of a variety of different particulates or pore forming agents, including inorganic salts. Preferably the particulate is insoluble in the solvent. The solvent may include dimethyl formamide (DMF), tetrahydrofuran (THF), dimethyacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water for the extraction, for example water at a temperature of about 60° C. The resulting pore diameter can also be substantially equal to the diameter of the salt grains.

The porous polymeric sheet can have a void-to-volume ratio from about 0.40 to about 0.90. Preferably the void-to-volume ratio is from about 0.65 to about 0.80. The resulting void-to-volume ratio can be substantially equal to the ratio of salt volume to the volume of the polymer plus the salt. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter is measured based on images from a scanning electron microscope (SEM). Formation of porous THORALON is described, for example, in U.S. Pat. No. 6,752,826 and 2003/0149471 A1, both of which are incorporated herein by reference.

Non-porous THORALON can be formed by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes/polycarbamates and urea linkages (hereinafter "—C(O)N or CON type polymers") may also be employed. These include CON type polymers that preferably include a soft segment and a hard segment. The segments can be combined as copolymers or as blends. For example, CON type polymers with soft segments such as PTMO, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

Preferably, the hard segment is formed from a diisocyanate and diamine. The diisocyanate may be represented by the formula OCN-R-NCO, where -R- may be aliphatic, aromatic, cycloaliphatic or a mixture of aliphatic and aromatic moieties. Examples of diisocyanates include MDI, tetramethylene diisocyanate, hexamethylene diisocyanate, trimethyhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3'-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible CON type polymers modified with cationic, anionic and aliphatic side chains may also be used. See, for example, U.S. Pat. No. 5,017,664.

Other biocompatible CON type polymers include: segmented polyurethanes, such as BIOSPAN; polycarbonate urethanes, such as BIONATE; and polyetherurethanes, such as ELASTHANE; (all available from POLYMER TECHNOLOGY GROUP, Berkeley, Calif.).

Other biocompatible CON type polymers can include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL -AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Application Publication No. 2002/0187288 A1, which is incorporated herein by reference.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

In another embodiment of the invention, the valve leaflet material is formed from or coated with a polyparaxylene ("parylene") or a parylene derivative, for example parylene C or parylene N. For example, the parylene or parylene derivative is created by first heating p-xylene or a suitable derivative at an appropriate temperature (for example, at about 950° C.) to produce the cyclic dimer di-p-xylylene (or a derivative thereof). The resultant solid can be separated in pure form, and then cracked and pyrolyzed at an appropriate temperature (for example, at about 680° C.) to produce a monomer vapor of p-xylylene (or derivative); the monomer vapor is cooled to a suitable temperature (for example, below 50° C.) and the leaflet formed by vapor phase deposition.

Attachment of the Valve Leaflets to the Support Structure

Another aspect of the present invention provides methods for attaching a valve leaflets to the support structure. The valve leaflet material can be attached to the support structure by any appropriate attachment means, including but not limited to, adhesive, fasteners, and tissue welding using heat and/or pressure. Alternatively, the valve leaflet may be formed on the support structure by an appropriate means, including but not limited to vapor deposition, spraying, electrostsatic deposition, ultrasonic deposition, or dipping.

In one embodiment of the invention, the valve prosthesis includes a valve leaflet formed from a non-porous biocompatible polyurethane based polymer such as non-porous THORALON. According to one method of attachment, a solution comprising a dissolved THORALON is coated and dried on a mandril to form a valve leaflet.

A solution for forming non-porous THORALON can be made by mixing the polyetherurethane urea (BPS-215) and the surface modifying additive (SMA-300) in a solvent, such as dimethyl formamide (DMF), tetrahydrofuran (THF), dimethyacetamide (DMAC), or dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments.

The entire composition can be cast as a sheet, or coated onto an article such as a mandril or a mold. In one example, the composition can be dried to remove the solvent. The mandril can be made from any suitable material that permits the THORALON to coated, dried on and removed from the mandril surface. Suitable materials include stainless steel and glass. In one embodiment, at least a portion of the outer surface of the mandril is formed in the desired shape of a valve leaflet. The valve leaflet can be formed by coating a thin layer of a solution of THORALON onto the shaped portion of the mandril, drying the coating of the THORALON on the mandril surface, and carefully removing the dried layer of THORALON.

One or more valve leaflets can be attached to the support frame by any suitable technique. In one embodiment, the valve leaflets comprise THORALON that is attached to the support frame by being formed around and encapsulating portions of the support frame. In one method, a solution comprising dissolved THORALON is sprayed and dried on an assembly formed by fitting at least a portion of the support frame over a mandril to form a valve prosthesis comprising one or more valve leaflets.

In one embodiment, one or more pre-coating layer(s) of THORALON are coated onto at least a portion of the mandril. Next, the support frame is fitted onto the mandril. The support frame can be any of those described above. Third, a solution comprising a DMAC solution of non-porous THORALON is coated onto the assembly comprising the mandril and the support frame using any suitable method, including spraying or dipping.

In one embodiment, a solution of THORALON is sprayed from a spray gun onto the assembly and the mandril is rotated during spraying process to promote uniform coating of the mandril. Any suitable rate of rotation can be used that provides for a uniform coating of the mandril and retains the coated material on the surface of the mandril. In one embodiment, the mandril is rotated at a rate of about 1 rpm.

When a pre-coating layer is present on the mandril, the THORALON adheres to the pre-coating layer as the solution of THORALON is spray coated onto the surface of the assembly and forms a sheet of THORALON that encapsulates portions of the support structure. Optionally, one or more bioactive agents can be coated onto the mandril with the THORALON.

In one embodiment, the pre-coating layer is first dried on the mandril, then the support frame is placed over the coated mandril, and finally second layer of THORALON is spray coated over the support frame as a solution comprising a suitable solvent such as DMAC and THORALON. The solvent in the spray solution preferably partially solubilizes the pre-coating layer so that one fused layer of THORALON is formed. The fused layer can encapsulate portions of the support frame and be solidified by evaporation of residual solvent, thereby joining the THORALON to the support frame. The residual solvent in the fused layer can be evaporated by heating the valve prosthesis on the mandril.

Alternatively, one or more valve leaflets can be attached to the support frame by other methods. In one embodiment, a sheet of material is cut to form a valve leaflet and the edges of the leaflet are wrapped around portions of a support frame and portions of the valve leaflet sealibly connected together to fasten the valve leaflet around the support frame. For example, one edge of a sheet of valve leaflet material can be wrapped around a portion of the support frame and held against the body of the valve leaflet, so that the valve leaflet material forms a lumen enclosing a portion of the support frame. A small amount of a suitable solvent is then applied to the edge of the valve leaflet material to dissolve the edge into an adjacent portion of the valve leaflet material and thereby seal the material around the support frame.

In another embodiment, the sheet of valve leaflet material is shaped to form the valve leaflet that is attached to a portion of a support frame using stitching through the valve leaflet material and around a portion of the support structure, adhesives, tissue welding or cross linking to directly join the valve leaflet material to the support frame. A valve leaflet attached to a support frame can be permitted to move relative to the support frame, or the valve leaflet can be substantially fixed in its position or orientation with respect to the support frame by using attachment configurations that resist relative movement of the valve leaflet and the support frame.

An electrostatic spray deposition (ESD) method of coating the valve leaflet material onto a mandril can also be used to form a valve leaflet. In this embodiment, particles in the sprayed solution of valve leaflet material are electrostatically charged when leaving the nozzle of the spray gun and the mandril is maintained at an electrical potential or grounded to attract the charged particles from the sprayed solution of valve leaflet material. The solution of valve leaflet material is first dissolved in a solvent and then sprayed onto the mandril using an ESD process.

The ESD process generally depends on the principle that a charged particle is attracted towards a grounded target. Without being confined to any theory, the typical ESD process may be described as follows. The solution that is to be deposited on the mandril is typically charged to several thousand volts (typically negative) and the mandril held at ground potential. The charge of the solution is generally great enough to cause the solution to jump across an air gap of several inches before landing on the target. As the solution is in transit towards the target, it fans out in a conical pattern which aids in a more uniform coating. In addition to the conical spray shape, the charged particles are further attracted towards the conducting portions of the target, rather than towards any non-conductive region of the target, leaving the coating mainly on the conducting regions of the target.

Generally, the ESD method allows for control of the coating composition and surface morphology of the deposited coating. In particular, the morphology of the deposited coating may be controlled by appropriate selection of the ESD parameters, as set forth in WO 03/006180 (Electrostatic Spray Deposition (ESD) of biocompatible coatings on Metallic Substrates), the contents of which are incorporated herein by reference. For example, a coating having a uniform thickness and grain size, as well as a smooth surface, may be obtained by controlling deposition conditions such as deposition temperature, spraying rate, precursor solution, and bias voltage between the spray nozzle and the medical device being coated. The deposition of porous coatings is also possible with the ESD method.

One hypothetical example of an electrostatic spraying apparatus and method is provided. Specifically, a solution of a non-porous THORALON material could be loaded into a 20 mL syringe of an ESD apparatus from Teronics Development Corp., which can then be mounted onto a syringe pump and connected to a tub that carries the solution to a spray head. The syringe pump could then used to purge the air from the solution line and prime the line and spray nozzle with solution. An electrical connection to the nozzle could supply the required voltage. An electrical connection could be provided to hold the mandril at grounding potential.

A motor could then be activated to rotate the mandril at a constant speed of about 1 rpm. The syringe pump could then be activated to supply the nozzle with a consistent flow of solution, and the power supply could be activated to provide a charge to the solution and cause the solution to jump the air gap and land on the mandril surface. As the coated surface is rotated away from the spray path, the volatile portion of the solution could be evaporated leaving a coating of THORALON behind. The mandril could be continually rotated in the spray pattern until the desired amount of non-porous THORALON material accumulates. During the coating process, the mandril could preferably be kept at ambient temperature and humidity, the solution could be pumped at a rate of about 2-4 $cm^3$/hr through the spray gun (which can be placed at a horizontal distance of approximately 6 cm from the mandril), and the bias voltage between the spray nozzle and the mandril should be approximately 10-17 kilovolts.

A support frame could then be slipped over a mandril (Teronics Development Corp., 2 mm×30 mm) so that at least a portion of the support frame makes an electrical connection with the mandril. The mandril could again be continually rotated in the spray pattern until the desired amount of non-porous THORALON material accumulates.

Where it is desired that portions of the perimeter of the valve leaflet material are not attached to the support frame, the valve leaflet material may be cut to free the material from the support frame. Alternatively, a mask may be used to cover portions of the support frame to prevent attachment of THORALON. The mask can be made from any suitable material that permits the THORALON to coated, dried on and removed from the mask surface. In one embodiment, a mask could be applied to the mandril surface before application of pre-coating layer(s) of THORALON. After the pre-coating layer(s) are applied, the mask could be removed and the support frame placed on the mandril. The mandril could again be continually rotated in the spray pattern until the desired amount of non-porous THORALON material accumulates. Only those portions of the support frame placed over portions of the mandril having a pre-coating of THORALON would be enclosed in THORALON.

Further examples of methods of preparation of valve prostheses, including methods of attaching a valve leaflet to a support frame, can be found in copending patent application attorney reference number 8627/654, entitled: Implantable Thromboresistant Valve, filed Jul. 25, 2005, Inventors: James D. Purdy, Jr. and Charles W. Agnew.

Bioactive Agents

Valve prosthesis of the present invention can include a bioactive agent. A bioactive agent can be included in any suitable part of the valve prosthesis, for example in the support frame and/or the valve leaflet. Selection of the type of bioactive agent, the portions of the valve prosthesis comprising the bioactive agent, and the manner of attaching the bioactive agent to the valve prosthesis can be chosen to perform a desired therapeutic function upon implantation and, in particular, to achieve controlled release of the bioactive agent.

For example, a therapeutic bioactive agent can be combined with a biocompatible polyurethane, impregnated in an extracellular collagen matrix material, incorporated in the support structure or coated over any portion of the valve prosthesis. In one embodiment, the valve prosthesis can comprise one or more valve leaflets comprising a bioactive agent coated on the surface of the valve leaflet or impregnated in the valve leaflet. In another aspect, a bioactive material is combined with a biodegradable polymer to form a portion of the support structure.

A bioactive agent can be incorporated in or applied to portions of the valve prosthesis by any suitable method that permits controlled release of the bioactive agent material and the effectiveness thereof for an intended purpose upon implantation in the body vessel. The configuration of the bioactive agent on or in the valve prosthesis will depend in part on the desired rate of elution for the bioactive agent. Bioactive agents can be coated directly on the valve prosthesis surface or can be adhered to a valve prosthesis surface by means of a coating. For example, a bioactive agent can be blended with a polymer and spray or dip coated on the valve prosthesis surface. For example, a bioactive agent material can be posited on the surface of the valve prosthesis and a porous coating layer can be posited over the bioactive agent material. The bioactive agent material can diffuse through the porous coating layer. Multiple porous coating layers and or pore size can be used to control the rate of diffusion of the bioactive agent material. The coating layer can also be non-porous wherein the rate of diffusion of the bioactive agent material through the coating layer is controlled by the rate of dissolution of the bioactive agent material in the coating layer.

The bioactive agent material can also be dispersed throughout the coating layer, by for example, blending the bioactive agent with the polymer solution that forms the coating layer. If the coating layer is biostable, the bioactive agent can diffuse through the coating layer. If the coating layer is biodegradable, the bioactive agent is released upon erosion of the biodegradable coating layer.

Bioactive agents may be bonded to the coating layer directly via a covalent bond or via a linker molecule which covalently links the bioactive agent and the coating layer. Alternatively, the bioactive agent may be bound to the coating layer by ionic interactions including cationic polymer coatings with anionic functionality on bioactive agent, or alternatively anionic polymer coatings with cationic functionality on the bioactive agent. Hydrophobic interactions may also be used to bind the bioactive agent to a hydrophobic portion of the coating layer. The bioactive agent may be modified to include a hydrophobic moiety such as a carbon based moiety, silicon-carbon based moiety or other such hydrophobic moiety. Alternatively, the hydrogen bonding interactions may be used to bind the bioactive agent to the coating layer.

The bioactive agent can optionally be applied to or incorporated in any suitable portion of the valve prosthesis. The bioactive agent can be applied to or incorporated in the valve prosthesis, a polymer coating applied to the valve prosthesis, a material attached to the valve prosthesis or a material forming at least a portion of the valve prosthesis. The bioactive agent can be incorporated within the material forming the support frame, or within pores formed in the surface of the support frame. The valve prosthesis can optionally comprise a coating layer containing the bioactive agent, or combinations of multiple coating layers configured to promote a desirable rate of elution of the bioactive from the valve prosthesis upon implantation within the body.

A coating layer comprising a bioactive agent can comprise a bioactive agent and a biostable polymer, a biodegradable polymer or any combination thereof. In one embodiment, the bioactive agent is blended with a biostable polymer to deposit the bioactive agent within the porous channels within the biostable polymer that permit elution of the bioactive agent from the valve prosthesis upon implantation. Alternatively, a blend of the bioactive and the bioabsorbable polymer can be incorporated within a biostable polymer matrix to permit dissolution of the bioabsorbable polymer through channels or pores in the biostable polymer matrix upon implantation in the body, accompanied by elution of the bioactive agent.

Multiple coating layers can be configured to provide a valve prosthesis with a desirable bioactive agent elution rate upon implantation. The valve prosthesis can comprise a diffusion layer positioned between a portion of the valve prosthesis that comprises a bioactive agent and the portion of the valve prosthesis contacting the body upon implantation. For example, the diffusion layer can be a porous layer positioned on top of a coating layer that comprises a bioactive agent. The diffusion layer can also be a porous layer positioned on top of a bioactive agent coated on or incorporated within a portion of the valve prosthesis.

A porous diffusion layer is preferably configured to permit diffusion of the bioactive agent from the valve prosthesis upon implantation within the body at a desirable elution rate. Prior to implantation in the body, the diffusion layer can be substantially free of the bioactive agent. Alternatively, the diffusion layer can comprise a bioactive agent within pores in the diffusion layer. Optionally, the diffusion layer can comprise a mixture of a biodegradable polymer and a bioactive positioned within pores of a biostable polymer of a diffusion layer. In another embodiment, the porous diffusion layer can comprise a mixture of a biodegradable polymer and a biostable polymer, configured to permit absorption of the biodegradable polymer upon implantation of the valve prosthesis to form one or more channels in the biostable polymer to permit an underlying bioactive agent to diffuse through the pores formed in the biostable polymer.

In one aspect of the invention, the bioactive agent is an antithrombogenic bioactive agent. Valve prostheses comprising an antithrombogenic bioactive agent are particularly preferred for implantation in areas of the body that contact blood. An antithrombogenic bioactive agent is any therapeutic agent that inhibits or prevents thrombus formation within a body vessel. The valve prosthesis can comprise any suitable antithrombogenic bioactive agent. Types of antithrombotic bioactive agents include anticoagulants, antiplatelets, and fibrinolytics. Anticoagulants are bioactive agents which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid is dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyridamole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Other examples of bioactive coating compounds include antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as (GP) $II_b/III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methyl-prednisolone, triamcinolone, betamethasone, and dexamethasone), non-steroidal agents (salicylic acid derivatives i.e. aspirin; para-aminophenol derivatives i. e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat. Still other bioactive agents that can be incorporated in or coated on a frame include a PPAR α-agonist, a PPAR δ agonist and RXR agonists, as disclosed in published U.S.

Patent Application US2004/0073297 to Rohde et al., published on Apr. 15, 2004 and incorporated in its entirety herein by reference.

Device Delivery and Methods of Treatment

The valve prosthesis as described herein can be delivered to any suitable body vessel, including a vein, artery, biliary duct, ureteral vessel, body passage or portion of the alimentary canal. Methods for delivering a valve prosthesis as described herein to any suitable body vessel are also provided, such as a vein, artery, biliary duct, ureteral vessel, body passage or portion of the alimentary canal. While many preferred embodiments discussed herein discuss implantation of a valve prosthesis in a vein, other embodiments provide for implantation within other body vessels. In another matter of terminology there are many types of body canals, blood vessels, ducts, tubes and other body passages, and the term "vessel" is meant to include all such passages.

In some embodiments, valve prostheses of the present invention having a compressed delivery configuration with a very low profile, small collapsed diameter and great flexibility, may be able to navigate small or tortuous paths through a variety of body vessels. A low-profile valve prosthesis may also be useful in coronary arteries, carotid arteries, vascular aneurysms, and peripheral arteries and veins (e.g., renal, iliac, femoral, popliteal, sublavian, aorta, intercranial, etc.). Other nonvascular applications include gastrointestinal, duodenum, biliary ducts, esophagus, urethra, reproductive tracts, trachea, and respiratory (e.g., bronchial) ducts. These applications may optionally include a sheath covering the valve prosthesis. In one aspect, the valve prostheses described herein are implanted from a portion of a catheter inserted in a body vessel.

Still other embodiments provide methods of treating a subject, which can be animal or human, comprising the step of implanting one or more valve prostheses as described herein. In some embodiments, methods of treating may also include the step of delivering a valve prosthesis to a point of treatment in a body vessel, or deploying a valve prosthesis at the point of treatment. Methods for treating certain conditions are also provided, such as venous valve insufficiency, varicose veins, esophageal reflux, restenosis or atherosclerosis. In some embodiments, the invention relates to methods of treating venous valve-related conditions.

A "venous valve-related condition" is any condition presenting symptoms that can be diagnostically associated with improper function of one or more venous valves. In mammalian veins, venous valves are positioned along the length of the vessel in the form of leaflets disposed annularly along the inside wall of the vein which open to permit blood flow toward the heart and close to prevent back flow. Two examples of venous valve-related conditions are chronic venous insufficiency and varicose veins.

In the condition of venous valve insufficiency, the valve leaflets do not function properly. For example, the vein can be too large in relation to the leaflets so that the leaflets cannot come into adequate contact to prevent backflow (primary venous valve insufficiency), or as a result of clotting within the vein that thickens the leaflets (secondary venous valve insufficiency). Incompetent venous valves can result in symptoms such as swelling and varicose veins, causing great discomfort and pain to the patient. If left untreated, venous valve insufficiency can result in excessive retrograde venous blood flow through incompetent venous valves, which can cause venous stasis ulcers of the skin and subcutaneous tissue. Venous valve insufficiency can occur, for example, in the superficial venous system, such as the saphenous veins in the leg, or in the deep venous system, such as the femoral and popliteal veins extending along the back of the knee to the groin.

The varicose vein condition consists of dilatation and tortuosity of the superficial veins of the lower limb and resulting cosmetic impairment, pain and ulceration. Primary varicose veins are the result of primary incompetence of the venous valves of the superficial venous system. Secondary varicose veins occur as the result of deep venous hypertension which has damaged the valves of the perforating veins, as well as the deep venous valves. The initial defect in primary varicose veins often involves localized incompetence of a venous valve thus allowing reflux of blood from the deep venous system to the superficial venous system. This incompetence is traditionally thought to arise at the saphenofemoral junction but may also start at the perforators. Thus, gross saphenofemoral valvular dysfunction may be present in even mild varicose veins with competent distal veins. Even in the presence of incompetent perforation, occlusion of the saphenofemoral junction usually normalizes venous pressure.

The initial defect in secondary varicose veins is often incompetence of a venous valve secondary to hypertension in the deep venous system. Since this increased pressure is manifested in the deep and perforating veins, correction of one site of incompetence could clearly be insufficient as other sites of incompetence will be prone to develop. However, repair of the deep vein valves would correct the deep venous hypertension and could potentially correct the secondary valve failure. Apart from the initial defect, the pathophysiology is similar to that of varicose veins.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously.

While the invention has been illustrated and described in detail in the drawings and foregoing description, the same is to be considered as illustrative and not restrictive in character, it being understood that only exemplary embodiments have been shown and described and do not limit the scope of the invention in any manner. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

We claim:

1. An artificial valve prosthesis for regulating fluid flow through a body vessel, comprising:
   a support structure comprising an outer frame defining a lumen and a transverse member traversing the lumen and dividing the lumen into a first lumen segment and a second lumen segment;
   a first valve leaflet and a second valve leaflet, wherein portions of a perimeter of the first valve leaflet and portions of a perimeter of the second valve leaflet are attached to the transverse member and to the outer frame proximally of the traverse member, and wherein portions of the perimeter of the first and the second valve leaflets are not attached to the transverse member or the outer frame, wherein the first valve leaflet is positioned within the first lumen segment and the second valve leaflet is positioned within the second lumen segment, and wherein the first and second valve leaflets are deformable between a first position allowing fluid flow in a first, antegrade, direction to a second position restricting fluid flow in a second, retrograde, direction.

2. The artificial valve prosthesis of claim 1, wherein fluid flow in the first, antegrade, direction in the first lumen segment occurs through an opening defined by the outer frame and the portion of the perimeter of the first valve leaflet not attached to the transverse member or the outer frame and in the second lumen segment occurs through an opening between the outer frame and the portion of the perimeter of the second valve leaflet not attached to the transverse member or the outer frame.

3. The artificial valve prosthesis of claim 1, wherein the support structure comprises a polymeric material.

4. The artificial valve prosthesis of claim 1, wherein the support structure comprises a material selected from a group consisting of stainless steel, nickel, silver, platinum, gold, titanium, tantalum, iridium, tungsten, a self-expanding nickel titanium alloy, and inconel.

5. The artificial valve prosthesis of claim 4, wherein the support structure comprises a self-expanding nickel titanium alloy.

6. The artificial valve prosthesis of claim 1, wherein the first valve leaflet and the second valve leaflet comprise a material selected from the group consisting of a synthetic biocompatible polymer, cellulose acetate, cellulose nitrate, silicone, polyethylene, teraphthalate, polyurethane, polyamide, polyester, polyorthoester, poly anhydride, polyether sulfone polycarbonate, polypropylene, high molecular weight polyethylene, a fluoroplastic material, polytetrafluoroethylene, or mixtures or copolymers thereof; polylactic acid, polyglycolic acid or copolymers thereof, a polyanhydride, polycaprolactone, polyhydroxy-butyrate valerate, polyhydroxyalkanoate, a polyetherurethane urea, naturally derived or synthetic collagenous material, an extracellular matrix material, submucosa, small intestinal submucosa, stomach submucosa, urinary bladder submucosa, uterine submucosa, renal capsule membrane, dura mater, pericardium, serosa, peritoneum or basement membrane materials, and liver basement membrane.

7. The artificial valve prosthesis of claim 1, where the first valve leaflet and the second valve leaflet comprise a bioremodelable material.

8. The artificial valve prosthesis of claim 1, wherein the first valve leaflet and the second valve leaflet comprise small intestinal submucosa.

9. The artificial valve prosthesis of claim 1, wherein the first valve leaflet and the second valve leaflet comprise a polyurethane.

10. An artificial valve prosthesis for regulating fluid flow through a body vessel, comprising:
a support structure comprising an outer frame defining a lumen and a plurality of radial members each having a first end and a second end, wherein the first ends of the plurality of radial members are joined within the lumen and wherein the second end of each of the plurality of radial members is attached to the outer frame at a position proximal of the first ends of the radial members;
a plurality of valve leaflets, wherein a first portion of a perimeter of each of the plurality of valve leaflets is attached to adjacent radial members, wherein a second portion of the perimeter of each of the plurality of valve leaflets extends between the adjacent radial members and wherein the plurality of valve leaflets form an enclosure having an proximal opening defined by the portions of the perimeter of the plurality of valve leaflets extending between the adjacent radial members,
wherein each of the plurality of valve leaflets is deformable between a first position allowing fluid flow in a first, antegrade, direction to a second position restricting fluid flow in a second, retrograde, direction.

11. The artificial valve prosthesis of claim 10, wherein the first ends of the plurality of radial members are joined at a common position within the lumen, wherein the second end of each of the plurality of radial members is attached to the outer frame at an equal proximal distance from the common position and wherein the second ends of the plurality of radial members are attached to the outer frame at positions equally spaced around a circumference of the outer frame.

12. The artificial valve prosthesis of claim 10, comprising three valve leaflets.

13. The artificial valve prosthesis of claim 10, wherein the support structure comprises a polymeric material.

14. The artificial valve prosthesis of claim 10, wherein the support structure comprises a material selected from a group consisting of stainless steel, nickel, silver, platinum, gold, titanium, tantalum, iridium, tungsten, a self-expanding nickel titanium alloy, and inconel.

15. The artificial valve prosthesis of claim 14, wherein the support structure comprises a self-expanding nickel titanium alloy.

16. The artificial valve prosthesis of claim 10, wherein the plurality of valve leaflets comprise a material selected from the group consisting of a synthetic biocompatible polymer, cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material, polytetrafluoroethylene, or mixtures or copolymers thereof; polylactic acid, polyglycolic acid or copolymers thereof, a polyanhydride, polycaprolactone, polyhydroxy-butyrate valerate, polyhydroxyalkanoate, a polyetherurethane urea, naturally derived or synthetic collagenous material, an extracellular matrix material, submucosa, small intestinal submucosa, stomach submucosa, urinary bladder submucosa, uterine submucosa, renal capsule membrane, dura mater, pericardium, serosa, peritoneum or basement membrane materials, and liver basement membrane.

17. The artificial valve prosthesis of claim 10, wherein the valve leaflets comprise a polyurethane or small intestinal submucosa.

18. An artificial valve prosthesis for regulating fluid flow through a blood vessel, comprising:
a support structure comprising an outer frame which defines a lumen with two ends and comprises a transverse member located near one end of the lumen and attached to the outer frame so as to divide the lumen into two portions,
two valve leaflets each having an end attached to the transverse member, an end partially attached to the outer frame near the end opposite the transverse member and two sides attached along a length of the outer frame proximally of the transverse member,
wherein the valve leaflets are deformable between a first position that permits fluid flow in an antegrade direction through the blood vessel and a second position that restricts fluid flow in a retrograde direction.

19. An artificial valve prosthesis for regulating fluid flow through a blood vessel, comprising:
   a support structure comprising an outer frame defining a lumen with a proximal end and a distal end,
   two valve leaflets attached along a portion of their perimeter to form a join, the join extending across the lumen near the distal end of the lumen so as to divide the lumen into two portions, each valve leaflet having leaflet end partially attached to the outer frame near the proximal end of the lumen and two sides attached along a length of the outer frame,
   wherein the valve leaflets are deformable between a first position that permits fluid flow in an antegrade direction through the blood vessel and a second position that restricts fluid flow in a retrograde direction.

20. A method of treating a subject, the method comprising: providing an artificial valve prosthesis comprising:
   a support structure comprising an outer frame defining a lumen and a transverse member traversing the lumen and dividing the lumen into a first lumen segment and a second lumen segment;
   a first valve leaflet and a second valve leaflet, wherein portions of a perimeter of the first valve leaflet and portions of a perimeter of the second valve leaflet are attached to the transverse member and to the outer frame proximally of the traverse member, and wherein portions of the perimeter of the first and the second valve leaflets are not attached to the transverse member or the outer frame,
   wherein the first valve leaflet is positioned within the first lumen segment and the second valve leaflet is positioned within the second lumen segment, and wherein the first and second valve leaflets are deformable between a first position allowing fluid flow in a first, antegrade, direction to a second position restricting fluid flow in a second, retrograde, direction,
   delivering the artificial valve prosthesis to a region of a body vessel in a compressed state; and
   deploying the artificial valve prosthesis in an expanded state.

* * * * *

UNITED STATES PATENT AND TRADEMARK OFFICE
CERTIFICATE OF CORRECTION

PATENT NO. : 7,503,928 B2
APPLICATION NO. : 11/582248
DATED : March 17, 2009
INVENTOR(S) : Brian C. Case et al.

It is certified that error appears in the above-identified patent and that said Letters Patent is hereby corrected as shown below:

In the Claims

Column 25, claim 1, line 2, before "member," delete "traverse" and substitute --transverse-- in its place.

Column 25, claim 6, line 37, after "polyorthoester," delete "poly anhydride" and substitute --polyanhydride-- in its place.

Column 26, claim 10, line 7, before "proximal opening" delete "an" and substitute --a-- in its place.

Column 26, claim 16, line 39, before "polyether sulfone," delete "poly anhydride" and substitute --polyanhydride-- in its place.

Column 28, claim 20, line 5, after "proximally of the" delete "traverse" and substitute --transverse-- in its place.

Signed and Sealed this

Eleventh Day of August, 2009

David J. Kappos
*Director of the United States Patent and Trademark Office*